US012629634B2

(12) United States Patent
Hoque et al.

(10) Patent No.: US 12,629,634 B2
(45) Date of Patent: May 19, 2026

(54) SILOXANE REMOVAL OFF LANDFILL GAS USING DIELECTRIC BARRIER DISCHARGE PLASMA

(71) Applicant: University of South Carolina, Columbia, SC (US)

(72) Inventors: Shamia Hoque, Irmo, SC (US); Tanvir Farouk, Irmo, SC (US); Malik M. Tahiyat, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 17/032,123

(22) Filed: Sep. 25, 2020

(65) Prior Publication Data

US 2021/0093999 A1    Apr. 1, 2021

Related U.S. Application Data

(60) Provisional application No. 62/906,279, filed on Sep. 26, 2019.

(51) Int. Cl.
B01D 53/75 (2006.01)
C07C 9/15 (2006.01)
C07F 7/08 (2006.01)

(52) U.S. Cl.
CPC .............. B01D 53/75 (2013.01); C07C 9/15 (2013.01); C07F 7/081 (2013.01); *B01D 2259/818* (2013.01)

(58) Field of Classification Search
CPC ..... C07C 9/15; C07F 7/081; B01D 2259/818;
B01D 53/75; B01D 2311/2615; B01J
12/002; B01J 2219/00635; B01J
2219/0894–2219/0898
See application file for complete search history.

(56) References Cited

U.S. PATENT DOCUMENTS

2007/0157884 A1*  7/2007  Hayashi ................ C23C 16/401
                                                            118/715
2008/0145553 A1*  6/2008  Boulos ................... B01J 19/088
                                                            118/620

FOREIGN PATENT DOCUMENTS

KR       20120033548 A  *  4/2012  ............ Y02W 30/20

OTHER PUBLICATIONS

Lovascio (PHD Thesis, University Pierre et Marie Curie 2010), Sara Lovascio. Cold Plasma deposition of organosilicon films with different monomers in a dielectric-barrier discharge. Chemical and Process Engineering. University Pierre et Marie Curie—Paris VI, 2010. (Year: 2010).*
KR20120033548A, Translation (Year: 2012).*
Twomey et al. (Plasma Process. Polym. 2007, 4 S450-S454), "Properties of Siloxane Coatings Deposited in a Reel-to-Reel Atmospheric Pressure Plasma System" (Year: 2007).*
Morent et al., Plasma Process. Polym. 2009, 6, S537-S542, "Plasma-Polymerization of HMDSO Using an Atmospheric Pressure Dielectric Barrier Discharge" (Year: 2009).*

(Continued)

*Primary Examiner* — Alexander W Keeling
(74) *Attorney, Agent, or Firm* — Douglas L. Lineberry

(57)          ABSTRACT
A dielectric barrier discharge system, employed to reform/remove organosilicon contaminants off a carrier stream to provide a sustainable, end-of-technology way of siloxane removal that will ensure siloxane does not re-enter the carrier stream, as well as generates useful end-products.

15 Claims, 7 Drawing Sheets

(56) References Cited

OTHER PUBLICATIONS

Boscher et al.("Influence of cyclic organosilicon precursors on the corrosion of aluminium coated sheet by atmospheric pressure dielectric barrier discharge", Surface & Coatings Technology, 205, 2011, pp. 5350-5357). (Year: 2011).*

Ooji et al.("DC Plasma Polymerization of Hexamethyldisiloxane", Plasma Chemistry and Plasma Processing, vol. 17, No. 2, 1997, pp. 123-154). (Year: 1997).*

* cited by examiner (a)                                             (b)

SILOXANE REMOVAL OFF LANDFILL GAS USING DIELECTRIC BARRIER DISCHARGE PLASMA

BACKGROUND

1) Technical Field

The present invention relates to a proposed dielectric barrier discharge system, employed to reform/remove organosilicon contaminants off a carrier stream.

2) Description of Related Art

Siloxanes constitute a group of low molecular weight volatile organosilicon (VOSC) polymers, which have widespread application in pharmaceutical, medical, cosmetic, and food production with a market size estimated to exceed $19 billion dollars by the end of 2017 with North America being among the top three consumers. Due to their potential toxic effects on the environment and health, siloxanes have been under investigation. Siloxanes have now become a completely different source of concern for industries providing alternative energy sources such as LFGTE (landfill gas to energy) projects.

A significant portion of siloxane containing products are deposited in landfill sites which are the source for LFG. Waste composition, humidity content, temperature and age influence the composition of landfill biogas. A significant portion (40-60%) of this LFG consists of methane, which is one of the major components of greenhouse gases. U.S. regulations have set a target of generating 25% of the energy from renewable sources by 2025, which is also a prime motivation of using LFG as an alternative energy source. However, LFG usage is hindered due to the presence of even trace siloxane(s) as contaminants. Siloxane compounds are detrimental to engines if these undergo combustion within a fuel mixture. Over extended periods of combustion, VOSCs dissociate to form silicon oxides, which deposit on engine components such as the crankshaft, cylinder-piston, and compressor blades and subsequently contribute towards erosion, seizing and reduction of the overall efficiency of engines. Besides adversely affecting the structure and performance of internal combustion engines, the presence of siloxane has also been reported to foul catalytic converters and degrade electrodes of fuel cells.

Currently, siloxane from LFG is removed through adsorption on activated carbon filters (ACF), which have limited regeneration ability. Silica gel and alumina are also being studied as potential alternatives with longer lifecycles, but these, like other adsorbents, suffer from the inability to desorb at low temperatures. Polyacrylic acid (PAA)-based polymer adsorbents are being investigated as a potential alternative with improved regeneration capabilities but they have lower capacity of adsorption compared to conventional silica gels. Usage of water as an absorbent has had limited effectiveness due to the low solubility of silicon compounds and the constant need for recycling; additionally, the absorption rate of water, being dependent on temperature, also incurs a high overhead cost. Both adsorption and absorption ultimately contributes to the waste cycle in the long run.

Accordingly, it is an object of the present invention to provide a dielectric barrier discharge (DBD) system to reform/remove organosilicon contaminants off a carrier stream. The system gives the opportunity for designing a sustainable end-of-technology way of siloxane removal that will ensure siloxane does not re-enter the carrier stream as well as generates useful end products.

SUMMARY

In a first embodiment, the current disclosure provides a dielectric barrier discharge system to remove organosilicon contaminants from a carrier stream. The system may include a carrier gas containing at least one siloxane, a dielectric barrier discharge reactor, a plasma stream, a cold trap, and the system may operate at atmospheric pressure and form polydimethylsiloxane (PDMS) deposits from the carrier gas. Further, carbon dioxide may be mixed with the plasma stream. Still, the at least one siloxane may comprise a methyl siloxane. Again, the methyl siloxane may comprise octamethylcyclotetrasiloxane or octamethyltrisiloxane. Still yet, the carrier gas may comprise helium. Again still, the system may include a helium feed. Further yet, the system may maintain ambient temperature. Further again, the system may have a flow rate of 400 to 500 sccm. Yet again, the system may produce solid phase deposits of PDMS as well as gaseous hydrocarbon fragments.

In a further embodiment, the current disclosure provides a method for removing organosilicon contaminants from a carrier stream. The method may include passing a carrier gas through at least one liquid siloxane to form a carrier gas/liquid siloxane stream, forming plasma in the carrier gas/liquid siloxane stream to form an effluent, passing the effluent through a cold trap, wherein polydimethylsiloxane deposits out from the effluent, and the method operates at atmospheric pressure. Still yet, the cold trap may contain a solvent. Further still, the solvent may comprise decane. Again yet, carbon dioxide may be mixed with the plasma stream. Still again, the at least one liquid siloxane may comprise a methyl siloxane. Again further, the methyl siloxane may comprise octamethylcyclotetrasiloxane or octamethyltrisiloxane. Yet still, the carrier gas may comprise helium. Furthermore, the method may operate at ambient temperature. Still again, the method may have a flow rate of 400 to 500 sccm. Once more, the method may produce solid phase deposits of PDMS as well as gaseous hydrocarbon fragments.

These and other aspects, objects, features, and advantages of the example embodiments will become apparent to those having ordinary skill in the art upon consideration of the following detailed description of example embodiments.

BRIEF DESCRIPTION OF THE DRAWINGS

The construction designed to carry out the disclosure will hereinafter be described, together with other features thereof. The disclosure will be more readily understood from a reading of the following specification and by reference to the accompanying drawings forming a part thereof, wherein an example of the disclosure is shown and wherein.

Figure 1:
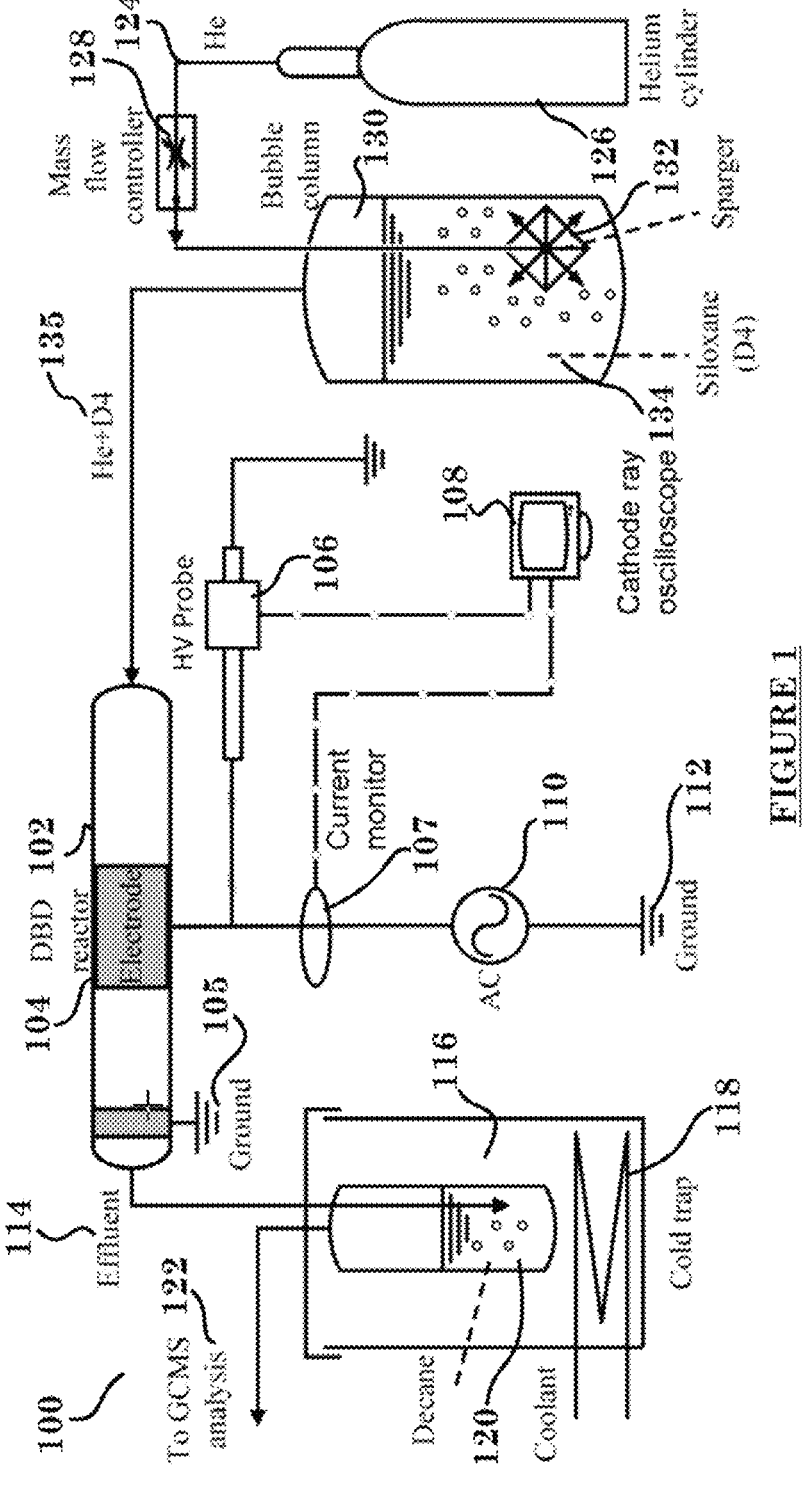
FIG. 1 shows a schematic representation of an experimental setup of the current disclosure.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF A PREFERRED EMBODIMENT

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further embodiment includes from the one particular value and/or to the other particular value. The recitation of numerical ranges by endpoints includes all numbers and fractions subsumed within the respective ranges, as well as the recited endpoints. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

Atmospheric pressure dielectric barrier discharge (DBD) plasma operating in a octamethylcyclotetrasiloxane (D4), octamethyltrisiloxane (L3)-helium mixture with and without carbon dioxide)-gas mixtures were studied as a prospective method for the reformation of the organosilicon compounds in a carrier stream. It was found that with the application of DBD, a significant amount of D4 precipitates out of the carrier stream in the form of a white residue on the reactor walls. Structural characterization of this residue with X-ray photoelectron and nuclear magnetic resonance spectroscopy revealed that the deposits are primarily composed of a linear chained polymerized form of D4 referred to as polydimethylsiloxane (PDMS). In case of L3, nearly all of the deposit consists of PDMS. The dependency of the carrier gas flow rate on the removal rate of D4 from the helium carrier gas was investigated for five different flow conditions. Solvent absorption with gas chromatography and mass spectrometry were used to deduce the concentration of D4 in the effluent from the reactor and hence the siloxane reformation ratio. A maximum of ~80% conversion of D4 in the helium stream was achieved.

All existing methods of removing siloxanes eventually end up in the waste cycle after the designated lifetimes. Pursuant to the current disclosure, siloxane is removed from the career gas by a chemical conversion to PDMS, which itself has a commercial market. Furthermore, DBD systems are conventionally robust with only the electrical connections or the mechanical integrity of the material of construction contributing to risk/safety factors. Thus, our system has a long time viability.

The current disclosure in one aspect examines non-equilibrium plasma discharges having large variance between the electron and neutral gas temperature possess high chemical selectivity, which is predominantly governed by the energetic electrons. Among the different non-equilibrium plasma systems, dielectric barrier discharge (DBD) maintains ambient temperature even at atmospheric pressure conditions, hence, chemical processes in DBD are typically driven by electrons and ions. The chemical selectivity of DBD systems has been applied for the removal of volatile organic compounds (VOC) such as, benzene and toluene with success. It has been demonstrated that DBD systems are capable of dissociating hydrocarbon compounds like formaldehyde, isopropanol, trichloroethylene, to more benign gaseous products like oxides of carbon and hydrogen. The mechanism of DBD primarily involves oxidation of the VOCs to less detrimental oxides of the constituent elements of the VOC molecule(s), a principle that can be utilized for VOSC treatment. In addition, DBD reactor cells are considered very robust and do not require periodic replacement and regeneration like filters and adsorbents, which appeals to an end user.

FIG. 1 shows a schematic representation 100 of an experimental setup of the current disclosure showing a DBD reactor 102 comprising an electrode 104 and a first ground 105 in association with an HV probe 106, a cathode ray oscilloscope 108, current monitor 107, AC source 110, and second ground 112. Effluent 114 may exit DBD reactor 102 to a cold trap 116 comprising coolant 118 and decane 120, once passing through, the effluent may exit to GCMS analysis 122. Helium feed 124 may be supplied by a helium cylinder 126 that flows through a mass flow controller 128 through a bubble column 130 comprising a Sparger 132 and a siloxane source 134 to generate loaded flow 135 that enters DBD reactor 102.

Description

A schematic of the experimental setup is presented in FIG. 1. Helium gas (Praxair UN1046) was bubbled through liquid 'Octamethylcyclotetrasiloxane (D4)' (99.8%, Sigma-Aldrich, $[—Si(CH_3)_2O—]_4$) in a bubble column. D4 was chosen as it is one of the most prevalent forms of siloxanes found in biogas from both landfill and anaerobic digesters. The resultant siloxane rich helium was passed through a tubular DBD reactor.

The DBD reactor was a borosilicate tube 120 mm long, 6.5 mm OD×5.2 mm ID. The exterior of the cylindrical reactor operated as the powered electrode with an electrode width of 25.4 mm. The plasma was formed in the helium-siloxane stream within the annular spacing of the reactor. The DBD was ignited and operated at steady state by a high voltage AC power supply (Information Unlimited, PVM 500). The applied voltage was measured with a 1000:1 high voltage probe (North Star, PVM-4) connected directly to the powered electrode and the current was measured with a Pearson current monitor (Model 6585). For all the experiments, a peak-to-peak voltage of ~23.6 kV was maintained at a frequency of ~23.4 kHz. The effluent from the plasma reactor was passed through a cold trap with Decane as a solvent for collecting the treated gas stream for further analysis.

A mass flow controller (MKS Instruments) was employed to maintain the flow rate of the helium stream for each experiment. Five different flow rates: 100, 200, 300, 400 and 500 sccm of helium were studied to investigate the effect of flow rate on the conversion rate of D4. Three replicate experiments were conducted for each flow rate, for a duration of one hour and both the reactor and the cold trap were examined thereafter. Control run(s) for each corresponding flow rate was conducted without having the plasma discharge activated.

The percentage of siloxane conversion/removal, between the siloxane treated and control runs was compared. For this purpose, the effluent from the plasma reactor was passed through a fixed volume of solvent (decane in this case) and then the mole fraction of the D4 in the resultant mixture was measured with a calibrated gas chromatograph mass spectroscopy (GCMS). The measured D4 mole fraction was compared with those of the control samples. The GCMS system consisted of HP 5890 (Agilent) gas chromatograph interfaced to V670S magnet sector mass spectrometer (Waters Inc.). The chromatography column used was a Rtx-5 (Restek) with a length of 30 m, ID of 0.25 mm and film thickness of 25 µm. Helium is used as carrier gas at a head pressure of 12 psi. 1 ml of acetone was mixed with 2 µl of the D4 dissolved decane solution and 1 µl of the resultant mixture was injected into the GC at a split ratio of 10:1. The GC was held at 50° C. for 3 mins and then ramped at 10° C./min to 300° C. The MS was scanned from 80-360 m/z.

Results and Advantages

Figure 2:
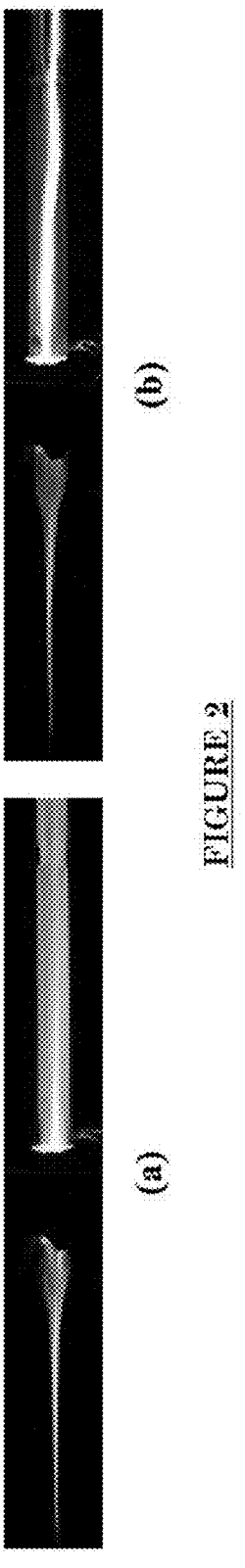
FIG. 2 shows a dielectric barrier discharge in operation.

FIG. 2 shows exemplar view of the dielectric barrier discharge in a stream of helium-siloxane (D4) mixture at different discharge power(s). In all cases, a whitish glow is observed typical of discharge in He with a bluish glow at the tip where the discharge extends to the atmosphere.

Figure 3:
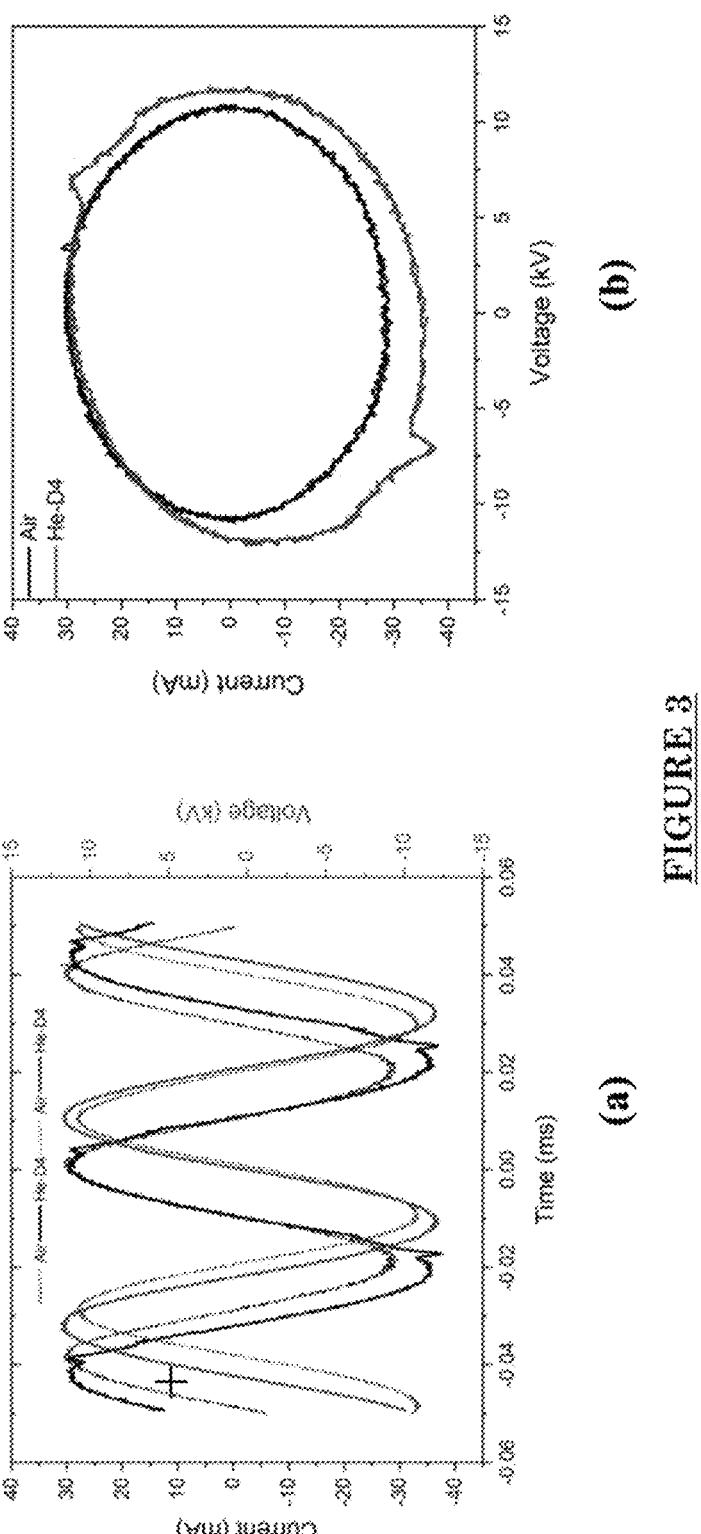
FIG. 3 at (a) shows waveforms of applied voltage and current for the He-D4 DBD discharge and air without any plasma and at (b) a Lissajous plot of current vs applied voltage for the same two cases.

The temporal evolution of the discharge voltage and current was measured to determine the plasma power. The profiles of current and voltage are shown at FIG. 3 at (a). The current waveform shows the presence of some periodic spikes, which could be due to the formation of filamentary streamers. No noticeable change in voltage and current waveforms were observed with variations in either flow rate or composition of the gaseous stream and experiment duration. To determine the capacitive current and power, the voltage and current profiles in air prior to breakdown was measured. The discharge power was calculated from the area under the V-I Lissajous plot, at FIG. 3 at (b) and was found to be ~12.7 W after subtracting the capacitive power. This plasma power was maintained in all the experiments.

Figure 4:
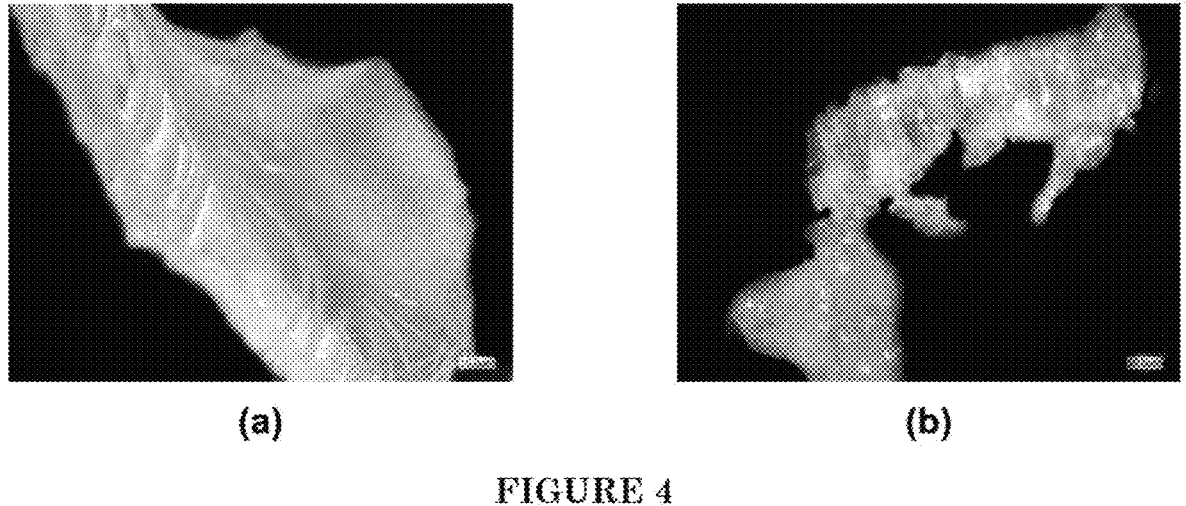
FIG. 4 shows exemplar optical images of reactor deposits.

A white deposit was observed to form on the inner walls of the reactor only when the DBD was powered on. FIG. 4 at (a) and (b) show the images of the reactor residue, observed under Keyence optical microscope. A predominantly whitish crystalline structure is observed, which was diagnosed by X-ray photoelectron spectroscopy to be Poly-di-methyl-siloxane (PDMS).

Figure 5:
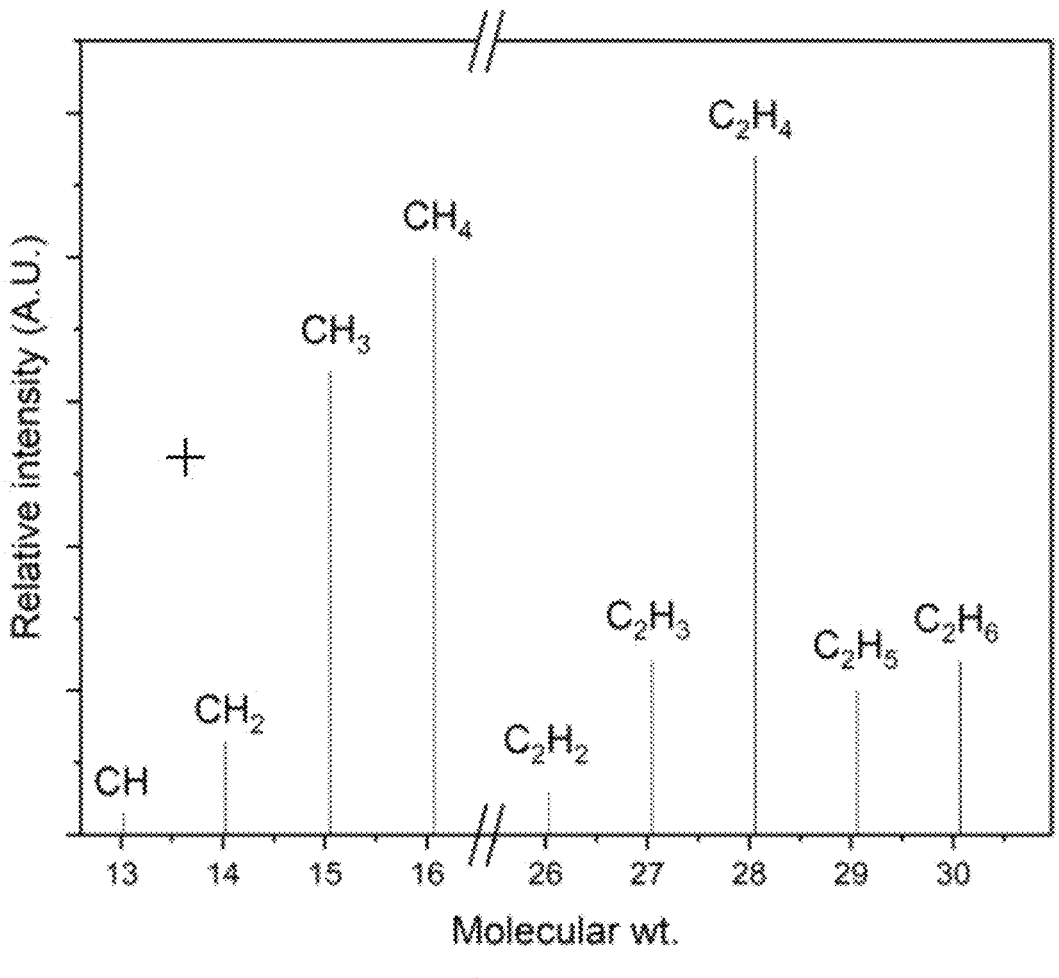
FIG. 5 shows a mass spectrum analysis of effluent.

The gaseous effluent of the plasma reactor was analyzed via a GCMS system. For this purpose, the GC was operated at room temperature and the MS was scanned from 10-110 m/z. The mass spectrum of the effluent is depicted in FIG. 5. Multiple hydrocarbon fragments were detected in the molecular weight range of 13 to 31, which corresponded to several fragmentations of methane and ethane molecules. Since the largest alkyl group present in the original D4 molecule is a methyl group, and the obtained mass spectrum shows traces of ethyl fragments, it is indicative that both bond splitting, as well as bond recombination reactions, took place during the plasma treatment of the gas stream.

Figure 6:
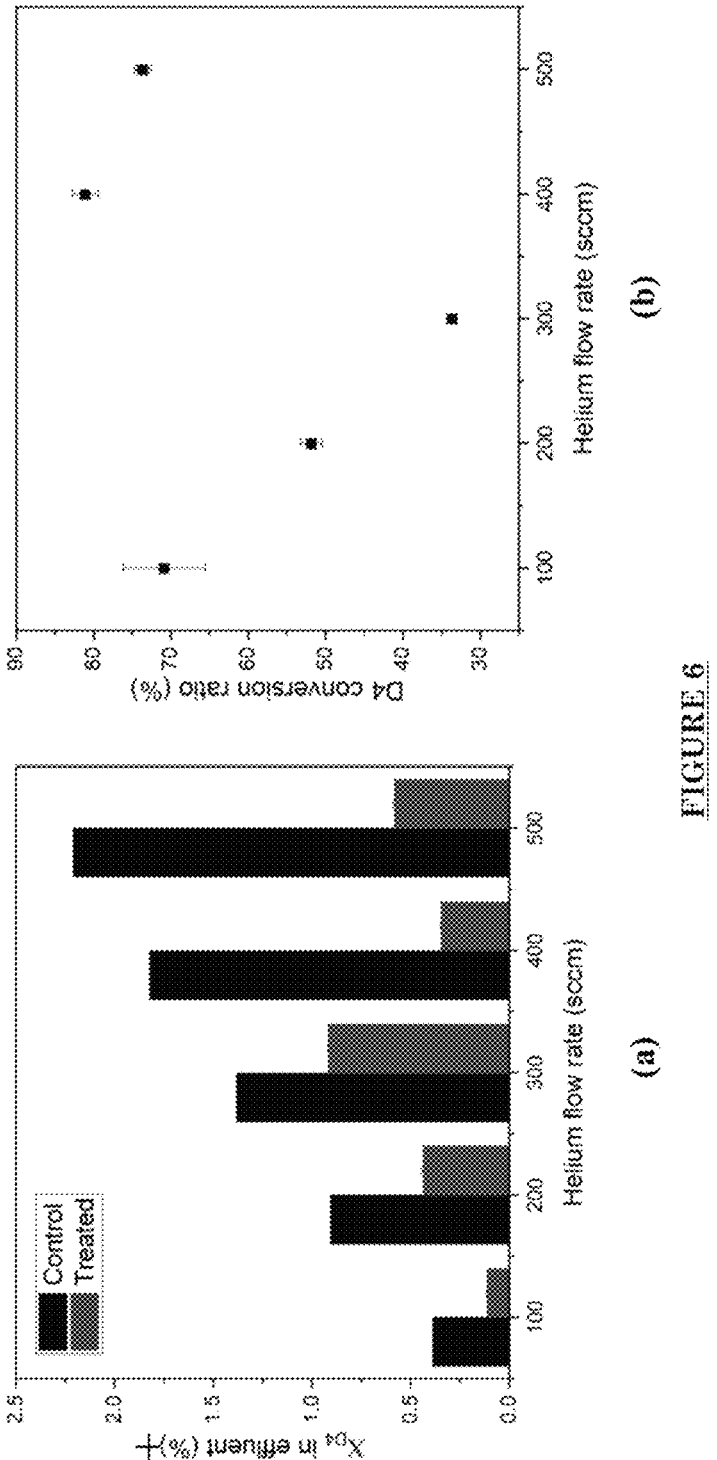
FIG. 6 shows a comparison of the concentration of D4 in the control and experimental samples (b) conversion percentage of D4.

FIG. 6 at (a) compares the concentration of siloxane in the effluent between the control and the plasma treated experiments. FIG. 6 at (b) summarizes the siloxane conversion percentage as a function of the helium flow rate. The siloxane concentration was determined through a GCMS analysis. The GCMS was calibrated with standard solutions of D4 siloxane (98%) in decane. A linear correlation between the normalized spectrum peaks, $$\left( A_{D4} = \frac{\text{Peak } Size_{D4}}{\text{Peak } Size_{D4} + \text{Peak } Size_{Decane}} \right)$$

and the siloxane mole fraction $$\left( X_{D4} = \frac{Moles_{D4}}{Moles_{D4} + Moles_{Decane}} \right)$$

was observed during the calibration. The cold trap decane (D4decane) samples from the plasma experiments were then analyzed in GCMS and the concentration of unreacted D4 was read off the correlation dataset. It is evident from the plots that D4decane in the plasma treated samples are considerably lower than that in control samples. The D4 removal fraction decreases linearly from ~70% to ~32% for flowrates of 100 sccm and 300 sccm and then increases to 80% for 400 sccm followed by a decrease for 500 sccm flowrate. The power required per gram of deposit ranged between 6.4-39.5 W/gm. It should be noted that each of the plasma treated experiments had a total runtime of one hour and within the operation time no significant changes in the discharge characteristics was observed. In addition, the electrodes remained operational after one hour.

As the flow rate is increased, the reaction time scales can start to become comparable to the reactor residence time resulting in insufficient plasma interaction time and thus, chemical conversion. Assuming the rate constant of electron impact reactions for D4 is similar to that of hexamethyld-isiloxane, the slowest electron impact reaction rate constant for D4 for an electron temperature of 5 eV is in the order of $10^{-9}$ cm$^3$/s. For an electron number density of $10^{10}$ cm$^{-3}$ the chemical reaction time ($\tau_{reaction}$) for the slowest reaction is estimated to be in the order of $10^{-2}$ s. The reactant mixture residence time ($\tau_{residence}$) through the annular reaction zone decreases from 0.30-0.06 s as the helium flow is increased from 100 to 500 sccm. Based on $\tau_{residence}$ and $\tau_{reaction}$, Damköhler number under laminar flow condition varies from 4.45 to 1.48 for flowrates of 100 sccm to 300 sccm indicating the slowest reaction time scales to be comparable to the flow residence time. It is interesting to note that as the flow rate is increased to 400 sccm, the removal rate increases again despite the fact that the flow residence decreases further; with a resultant laminar Da number of 1.11 and 0.89 for 400 sccm and 500 sccm respectively. Even though the flow rates considered result in a laminar flow regime, preliminary simulations show that for flow rates from 400 to 00 sccm localized flow reversal and recirculation zones are formed/triggered by variation in the wall morphology resulting from wall surface deposits. These recirculation zones increase localized residence time allowing the reactants to participate in the reaction process for longer duration. For flow rates ranging from 400 to 500 sccm the extent of the recirculation regions increases significantly. As a result, despite a decrease in the Da number in the bulk flow field the localized high residence time region contributes to the increased conversion.

FIG. 6 shows at (a) a comparison of the concentration of D4 in the control and experimental samples and at (b) a conversion percentage of D4.

An atmospheric pressure dielectric barrier discharge was employed in reforming siloxane in a carrier gas stream. Siloxane exposed to plasma results in both solid phase deposits of PDMS and gaseous hydrocarbon fragments. The conversion percentage ranged from 30-80% depending on the flowrates of the career gas. This technology also has the potential of converting the main components of LFG, meth-

US 12,629,634 B2

Figure 7:
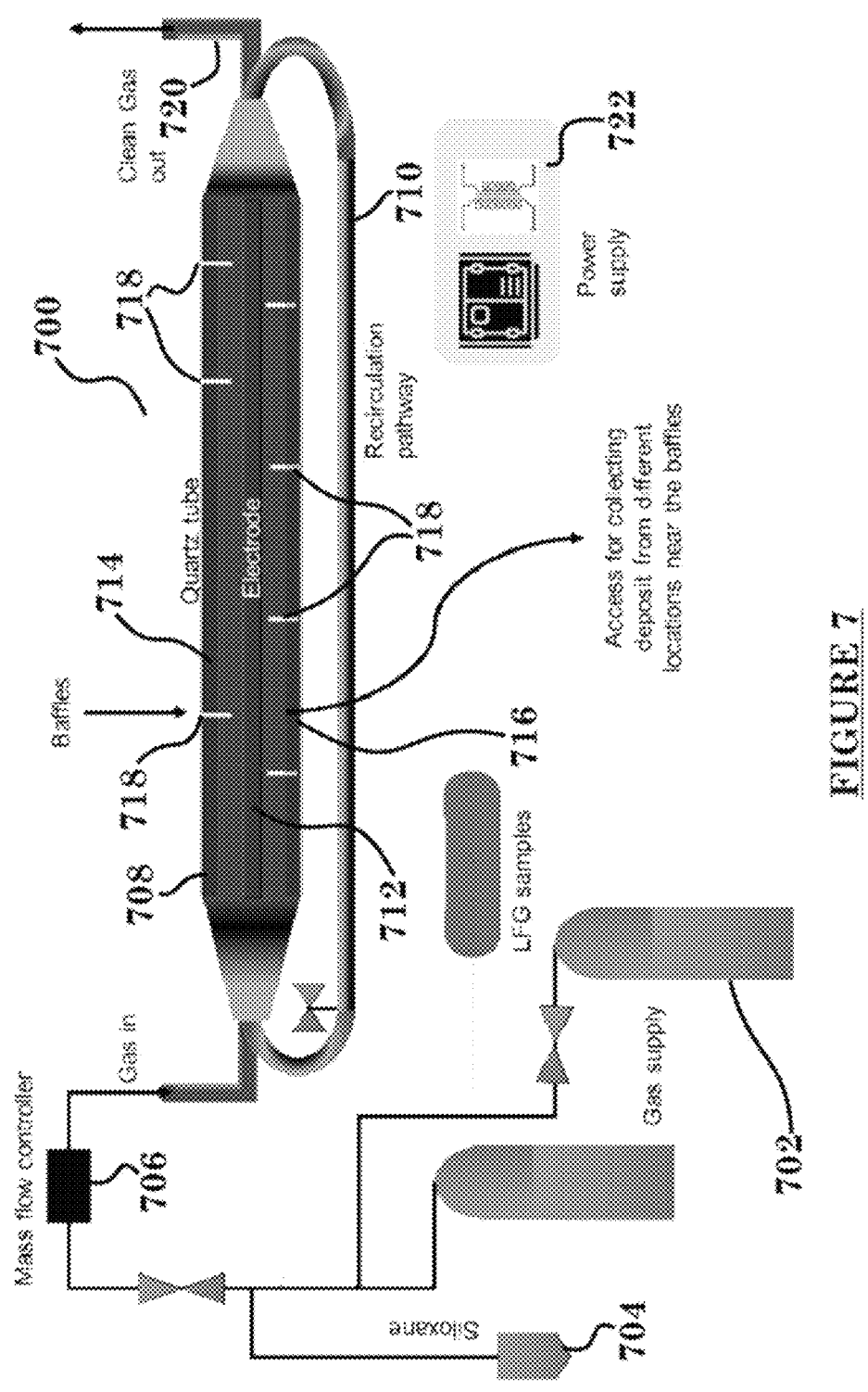
FIG. 7 shows a schematic of a prototype of one embodiment of the current disclosure.

9 ane and carbon dioxide to a higher caloric gas, syngas (carbon monoxide and hydrogen). A prototype 700 is currently under design for fabrication as shown in FIG. 7. The setup, in one aspect, may include a gas supply 702, siloxane source 704, a mass flow controller 706, a reactor 708 with a recirculation pathway 710, electrode 712, quartz tube 714, access 716 for collecting deposits from different locations near baffles 718 and a clean out gas supply 720 and associated power supply 722.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A dielectric barrier discharge system to remove organo-silicon contaminants from a carrier stream comprising:
    a carrier gas containing at least one siloxane or helium but no oxygen;
    a dielectric barrier discharge reactor comprising a quartz tube and forming a cylindrical shaped reactor with at least one electrode surrounding the cylindrical shaped reactor;
    a plasma stream;
    a cold trap;
    a recirculation pathway;
    wherein the system operates at atmospheric pressure and the dielectric barrier discharge reactor is configured with at least one inner wall of the dielectric barrier discharge reactor configured to form irregularly shaped crystalline polydimethylsiloxane (PDMS) deposits on at least one inner wall surface of the reactor thereby forming at least one wall morphology on the at least one inner wall surface wherein a shape of the at least one wall morphology forms localized reversal and recirculation zones inside the dielectric barrier discharge reactor to increase localized residence time and increase PDMS conversion when a flow rate for the carrier gas ranges from 400 to 500 seem; and
    wherein the carrier gas containing at least one siloxane is diverted along the recirculation pathway to reenter the dielectric barrier discharge reactor to yield a PDMS conversion range of from 30 to 80%.

2. The system of claim 1, further comprising carbon dioxide mixed with the plasma stream.

3. The system of claim 1, wherein the at least one siloxane comprises a methyl siloxane.

4. The system of claim 3, wherein the methyl siloxane comprises octamethylcyclotetrasiloxane or octamethyltrisi-loxane.

5. The system of claim 1, further comprising a helium feed.

6. The system of claim 1, wherein the system maintains ambient temperature.

7. The system of claim 1, wherein the system produces solid phase deposits of PDMS as well as gaseous hydrocarbon fragments.

8. A method for removing organosilicon contaminants from a carrier stream comprising:
    passing a carrier gas through at least one liquid siloxane or helium but no oxygen to form a carrier gas/liquid siloxane stream;
    forming plasma in the carrier gas/liquid siloxane stream to form an effluent;
    passing the effluent through a cold trap;
    wherein irregularly shaped polydimethylsiloxane deposits out from the effluent in a dielectric bani er discharge reactor configured with at least one inner wall of the dielectric barrier discharge reactor configured to form polydimethylsiloxane deposits from the carrier gas/liquid siloxane stream directly onto the at least one inner wall of the dielectric barrier discharge reactor thereby forming at least one wall morphology on the at least one inner wall surface wherein a shape of the at least one wall morphology forms localized flow reversal and recirculation zones inside the dielectric barrier discharge reactor to increase localized residence time and increase PDMS conversion when a flow rate for the carrier gas ranges from 400 to 500 seem;
    configuring the dielectric barrier discharge reactor to comprise a quartz tube and forming a cylindrical shaped reactor with at least one electrode surrounding the cylindrical shaped reactor;
    wherein the method operates at atmospheric pressure;
    wherein the carrier gas containing at least one siloxane is diverted along a recirculation pathway to reenter the dielectric barrier discharge reactor to yield a PDMS conversion range of from 30 to 80%.

9. The method of claim 8, wherein the cold trap contains a solvent.

10. The method of claim 9, wherein the solvent comprises decane.

11. The method of claim 8, further comprising mixing carbon dioxide with the plasma stream.

12. The method of claim 8, wherein the at least one liquid siloxane comprises a methyl siloxane.

13. The method of claim 12, wherein the methyl siloxane comprises octamethylcyclotetrasiloxane or octamethyltrisi-loxane.

14. The method of claim 8, wherein the method operates at ambient temperature.

15. The method of claim 8, further comprising producing solid phase deposits of PDMS as well as gaseous hydrocarbon fragments.

* * * * *